(12) United States Patent
Chait et al.

(10) Patent No.: US 12,262,978 B2
(45) Date of Patent: Apr. 1, 2025

(54) ABSOLUTE BLOOD VOLUME ESTIMATION DEVICE AND METHOD

(71) Applicants: University of Massachusetts, Boston, MA (US); Analiza, Inc., Cleveland, OH (US); Medical University of Graz, Graz (AT)

(72) Inventors: Yossi Chait, Longmeadow, MA (US); Joseph Horowitz, Amherst, MA (US); Christopher V. Hollot, East Hampton, MA (US); Hamed Samandari, Mason, OH (US); Michael J. Germain, Hampden, MA (US); Daniel Schneditz, Graz (AT)

(73) Assignees: University of Massachusetts, Boston, MA (US); Analiza, Inc., Cleveland, OH (US); Medical University of Graz, Graz (AT)

( * ) Notice: Subject to any disclaimer, the term of this patent is extended or adjusted under 35 U.S.C. 154(b) by 0 days.

(21) Appl. No.: 18/400,507

(22) Filed: Dec. 29, 2023

(65) Prior Publication Data

US 2024/0131239 A1 Apr. 25, 2024

Related U.S. Application Data

(62) Division of application No. 16/617,904, filed as application No. PCT/US2018/035676 on Jun. 1, 2018, now Pat. No. 11,896,748.

(Continued)

(51) Int. Cl.
*A61B 5/02* (2006.01)
*A61B 5/00* (2006.01)
(Continued)

(52) U.S. Cl.
CPC ........ *A61B 5/02028* (2013.01); *A61B 5/0275* (2013.01); *A61B 5/14535* (2013.01);
(Continued)

(58) Field of Classification Search
CPC .... A61M 1/1613; A61M 1/267; A61M 1/361; A61M 2205/3389; A61M 2205/50;
(Continued)

(56) References Cited

U.S. PATENT DOCUMENTS

| | | |
|---|---|---|
| 5,326,476 A | 7/1994 | Grogan et al. |
| 6,246,894 B1 | 6/2001 | Steuer et al. |

(Continued)

FOREIGN PATENT DOCUMENTS

| | | |
|---|---|---|
| WO | WO-0247609 A2 | 6/2002 |
| WO | WO-2014204841 A1 | 12/2014 |

(Continued)

OTHER PUBLICATIONS

"U.S. Appl. No. 16/545,184, Examiner Interview Summary mailed Apr. 26, 2022", 2 pgs.

(Continued)

*Primary Examiner* — John Kim
(74) *Attorney, Agent, or Firm* — Schwegman Lundberg & Woessner, P.A.

(57) ABSTRACT

Absolute blood volume in dialysis patients is a useful patient attribute to know for dialysis treatment, diagnosis, adjustments, etc. In some cases, it is difficult or impossible to directly determine absolute blood volume. Estimating absolute blood volume may be used to overcome the inability to directly determine the absolute blood volume. Estimating absolute blood volume may include obtaining a series of measurements of hemoconcentration of a patient over a time period, and estimating parameters for a physiological model based on the series of measurements. The absolute blood (Continued)

volume of the patient may be determined using the physiological model.

11 Claims, 8 Drawing Sheets

Related U.S. Application Data

(60) Provisional application No. 62/514,322, filed on Jun. 2, 2017.

(51) Int. Cl.
    *A61B 5/0275*     (2006.01)
    *A61B 5/145*     (2006.01)
    *A61M 1/16*     (2006.01)
    *A61M 1/26*     (2006.01)
    *A61M 1/36*     (2006.01)

(52) U.S. Cl.
    CPC ......... *A61B 5/6866* (2013.01); *A61M 1/1613* (2014.02); *A61M 1/267* (2014.02); *A61M 1/361* (2014.02); *A61M 2205/3389* (2013.01); *A61M 2205/50* (2013.01); *A61M 2205/52* (2013.01); *A61M 2230/20* (2013.01); *A61M 2230/207* (2013.01)

(58) Field of Classification Search
    CPC .......... A61M 2205/52; A61M 2230/20; A61M 2230/207; A61B 5/02028; A61B 5/0275; A61B 5/14535; A61B 5/6866
    See application file for complete search history.

(56) References Cited

U.S. PATENT DOCUMENTS

| | | |
|---|---|---|
| 2002/0085951 A1 | 7/2002 | Gelfand et al. |
| 2009/0101577 A1 | 4/2009 | Fulkerson et al. |
| 2020/0054814 A1 | 2/2020 | Abohtyra et al. |
| 2020/0086027 A1 | 3/2020 | Chait et al. |

FOREIGN PATENT DOCUMENTS

| | | |
|---|---|---|
| WO | WO-2015179401 A1 | 11/2015 |
| WO | WO-2015179523 A1 | 11/2015 |
| WO | WO-2018223046 A1 | 12/2018 |

OTHER PUBLICATIONS

"U.S. Appl. No. 16/545,184, Final Office Action mailed Apr. 6, 2022", 13 pgs.
"U.S. Appl. No. 16/545,184, Non Final Office Action mailed Oct. 18, 2022", 12 pgs.
"U.S. Appl. No. 16/545,184, Non Final Office Action mailed Nov. 23, 2021", 9 pgs.
"U.S. Appl. No. 16/545,184, Response filed Mar. 23, 2022 to Non Final Office Action mailed Nov. 23, 2021", 12 pgs.
"U.S. Appl. No. 16/545,184, Response filed Oct. 5, 2022 to Final Office Action mailed Apr. 6, 2022", 14 pgs.
"U.S. Appl. No. 16/617,904, Ex Parte Quayle Action mailed Jul. 24, 2023", 4 pgs.
"U.S. Appl. No. 16/617,904, Non Final Office Action mailed Oct. 13, 2022", 15 pgs.
"U.S. Appl. No. 16/617,904, Notice of Allowance mailed Sep. 27, 2023", 6 pgs.
"U.S. Appl. No. 16/617,904, Preliminary Amendment filed Nov. 27, 2019", 5 pgs.
"U.S. Appl. No. 16/617,904, Response filed Apr. 12, 2023 to Non Final Office Action mailed Oct. 13, 2022", 10 pgs.
"U.S. Appl. No. 16/617,904, Response filed Sep. 12, 2023 to Ex Parte Quayle Action mailed Jul. 24, 2023", 4 pgs.
"U.S. Appl. No. 16/617,904, Response filed Sep. 16, 2022 to Restriction Requirement mailed Jul. 18, 2022", 8 pgs.
"U.S. Appl. No. 16/617,904, Restriction Requirement mailed Jul. 18, 2022", 9 pgs.
"BVM—Blood Volume Monitor", Fresenius Medical Care, [Online]. [Accessed May 23, 2018]. Retrieved from the Internet: <URL: http://fmc-au.com/pdf/machines/Blood%20Volume%20Monitor-Literature.pdf>, (2012), 14 pgs.
"European Application Serial No. 18808915.5, Extended European Search Report mailed Feb. 9, 2021", 5 pgs.
"European Application Serial No. 18808915.5, Resposne filed Aug. 17, 2021 to Extended European Search Report mailed Feb. 9, 2021", 24 pgs.
"International Application Serial No. PCT/US2018/035676, International Preliminary Report on Patentability mailed Dec. 12, 2019", 9 pgs.
"International Application Serial No. PCT/US2018/035676, International Search Report mailed Aug. 29, 2018", 2 pgs.
"International Application Serial No. PCT/US2018/035676, Written Opinion mailed Aug. 29, 2018", 7 pgs.
Anne, Diroll, "Fluid Management during Hemodialysis", NANT convention, available from the internet, (2016), 47 pgs.

ABSOLUTE BLOOD VOLUME ESTIMATION DEVICE AND METHOD

CROSS-REFERENCE TO RELATED APPLICATION

This application is a continuation U.S. patent application Ser. No. 16/617,904 filed on Nov. 27, 2019, now U.S. Pat. No. 11,896,748, which is a U.S. National Stage Filing under 35 U.S.C. 371 from International Application No. PCT/US2018/035676 filed on Jun. 1, 2018, which claims the benefit of priority to U.S. Provisional Patent Application Ser. No. 62/514,322 filed Jun. 2, 2017, the entire contents of which are hereby incorporated by reference herein in their entirety.

STATEMENT REGARDING FEDERALLY SPONSORED RESEARCH OR DEVELOPMENT

This invention was made with government support under DK096006 awarded by National Institutes of Health (NIH). The government has certain rights in the invention.

BACKGROUND

Long- and short-term adverse outcomes in dialysis have been associated with intradialytic hypotension, a common dialysis complication and significant cause of morbidity. Knowledge of absolute blood volume (ABV) may be used to significantly improve treatment outcomes. Different dilution-based protocols have been proposed for estimating ABV, which rely on the classic mono-exponential back-extrapolation algorithm (BEXP), which may be inaccurate or have too wide of an error range to be useful.

Current dialysis machine technology provides online sensors such as the CRIT-LINE of Fresenius Medical Care, Waltham, MA and a blood volume monitor (BVM), such as that of Fresenius Medical Care, Schweinfurt, Germany, to measure the concentration of blood components. The sensor derives patients' hematocrit and oxygen saturation using photo-optical technology. The BVM derives blood water concentration (BWC) and estimates hematocrit using ultrasonic technology and temperature measurements. In addition, both sensors provide estimates for the percent change in a patient's intravascular blood volume—referred to as relative blood volume (RBV). RBV estimates reported by these sensors are based on a single compartment assumption. However, ABV, the crucial piece of information, cannot be inferred from RBV alone. Patients with differing ABVs can exhibit similar RBVs.

In recent years, in attempting to find a practical approach to translate the RBV information into ABV information, researchers' attention has been directed toward dilution techniques that can use the available measurements by the sensors. A recent study showed that ultra-pure dialysate, which is readily available in online hemodiafiltration, can be used as a dilution medium to make estimates of ABV. In this technique, a bolus injection of ultra-pure dialysate was administered within the treatment. The online measurement of BWC by the BVM, in conjunction with the back-extrapolation (BEXP) algorithm, was used to estimate the initial BWC at the time of injection. This estimate together with the size of the bolus injection was then used to estimate ABV at the time of injection.

The BEXP algorithm, which fits an exponential function to a measured indicator, is a standard pharmacokinetic approach that assumes that the indicator dynamics can be sufficiently represented by a single-compartment model with constant coefficients. However, studies have shown that the distribution of an indicator is not uniform within the bloodstream especially during the initial phase due to blood flow, and researchers have considered models consisting of more than one compartment to better reflect such distribution. Multi-compartment modelling has been studied, including fixed-volume, variable-volume, and parallel and series compartment configurations. Applications of such models include the distribution of indicators in solute kinetics, hemodialysis, β2-microglobulin kinetics, indocyanine green distribution in blood, and urea kinetics. However, application of high-order compartmental models, such as models described in some studies involve an increasing number of unknown parameters, resulting in a difficult, if not impossible, estimation problem. Because of such limitations, these techniques have not been incorporated into day-to-day clinical practice.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
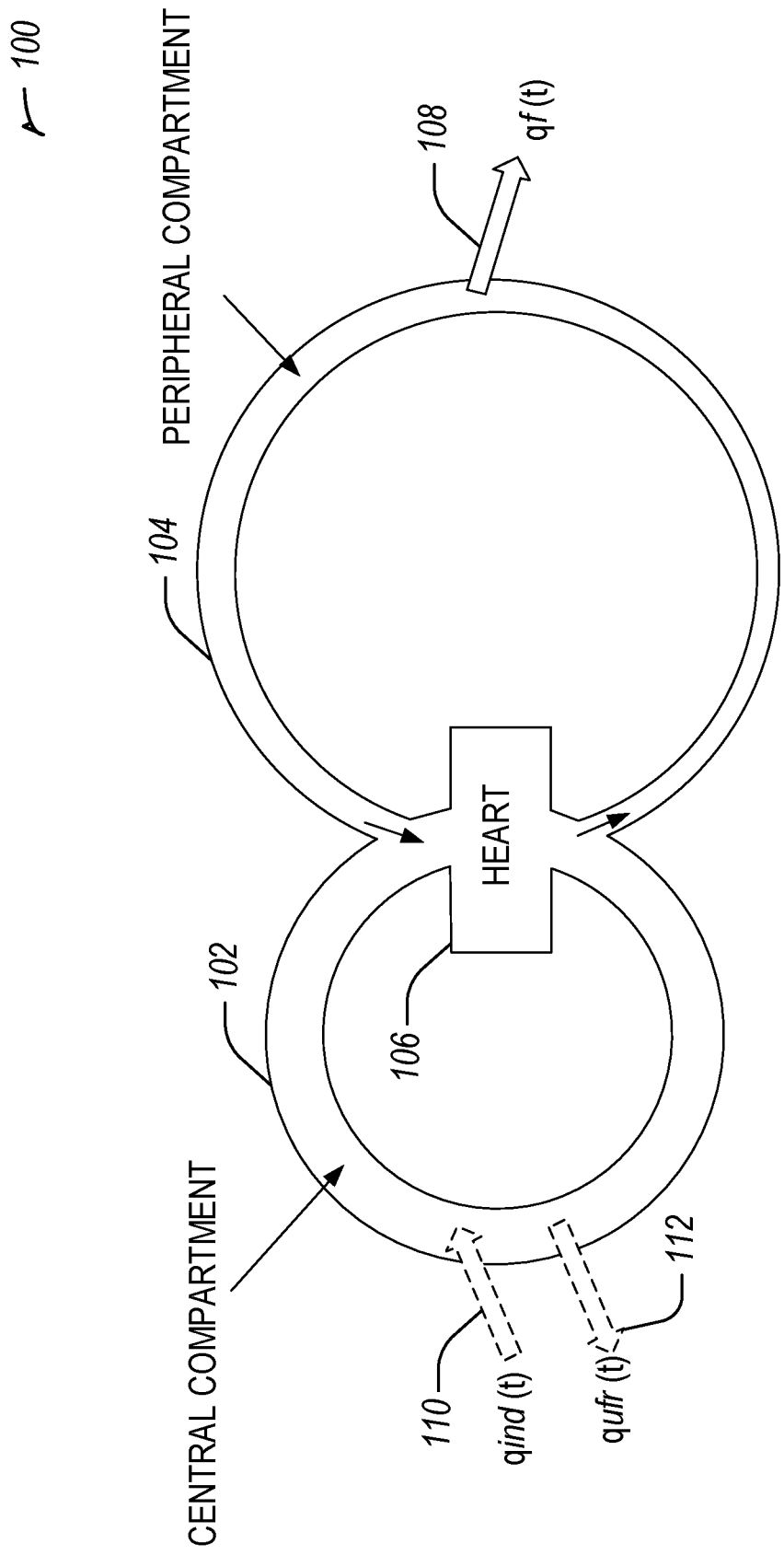
FIG. 1 illustrates a schematic diagram of a variable volume two-compartment, intravascular blood-water model in accordance with some embodiments.

The systems and methods described herein include a new, physiologically motivated, variable-volume, two-compartment model as the basis for estimating absolute blood volume (ABV). The model is uniquely configured to achieve a better balance between complexity, identifiability, and precision. Absolute blood volume estimates derived from this model are compared with estimates from the classic mono-exponential back-extrapolation algorithm.

Volume management plays an important role in renal replacement therapies. Removing too much fluid by ultrafiltration triggers intradialytic hypotension, a significant cause of long- and short-term adverse outcomes, while removing too little fluid causes edema, left ventricular hypertrophy and heart failure. Knowing a patient's ABV at the start of ultrafiltration may allow clinicians to better guide fluid balance within a dialysis treatment and return patients to their dry weight, improving dialysis outcomes significantly. The current techniques directly measuring ABV, isotope dilution, is invasive, expensive, time consuming, and impractical for routine clinical application. Estimating the ABV using the techniques described herein avoids the difficulties of direct measurement while maintaining sufficient accuracy.

The technique described herein includes a dialysate dilution protocol and an estimation technique based on a variable volume, two-compartment, intravascular blood water content kinetic model (VVKM). Clinical testing showed that distribution of differences between ABV estimated from the VVKM and the BEXP techniques showed negligible systematic difference between the mean values of ABVs estimated, and that the VVKM estimates were 53% and 42% more precise for the CV and AV patients, respectively. Good agreement was observed between measured and VVKM-estimated blood water concentration (BWC) with the root-mean-square error (RMSE) less than 0.02 kg/kg (2%) and 0.03 kg/kg (3%) for AV and CV patients, respectively. The dilution protocol and the VVKM-based estimation technique offer a noninvasive, inexpensive, safe, and practical approach for ABV estimation in routine dialysis settings.

A dialysis machine (hemodialysis, hemodiafiltration, and other variations) including sensors for measuring hematocrit and BWC (the latter of which may be to calculate RBV changes) may be used to perform the VVKM technique. Dialysate may be delivered, for example at a flow of either 500 or 800 mL/min, and at a temperature, such as 36 degrees C. Extracorporeal blood flows, substitution fluid infusion rates, and ultrafiltration rates may be maintained constant within each treatment. Dialysate [Na+] and diaysis pre- or post-dilution configuration may be set as previously prescribed. Mean substitution volume may be 5 L.

Indicator dilutions may be administered, such as by using a bolus function in a dialysis machine. This function may deliver ultrapure dialysate, such as in multiples of 30 mL at a constant infusion rate of approximately 150 mL/min during the dialysis session. This bolus volume may be delivered with an accuracy of better than ±1.5%. During infusion lasting about 1 to 2 min depending on the magnitude of the bolus volume, the dialysis machine may automatically reduce the blood flow rate to prevent an excessive increase in venous line pressure but maintained all ultrafiltration and infusion rates.

FIG. 1 illustrates a schematic diagram 100 of a variable volume two-compartment, intravascular blood-water model in accordance with some embodiments. The schematic diagram 100 shows a first compartment 102 (e.g., a central compartment) and a second compartment (e.g., a peripheral compartment 104). The first and second compartments 102 and 104 mix in a mixing compartment 106 (e.g., a heart compartment, portion, or a space). The schematic diagram 100 of the variable volume two-compartment, intravascular blood-water model includes a $q_{ufr}(t)$, ultrafiltration rate 112, a $q_{ind}(t)$, indicator infusion rate 110, a $q_f(t)$, refiling/filtration rate 108, and $q_1(t)$ and $q_2(t)$, blood exchange between compartments.

The intravascular circulatory system may be modeled by the first and second compartments 102 and 104, which may be termed central and peripheral, respectively. In an example, the central compartment may model central parts of the intravascular volume including the heart, central veins and arteries, and lungs. This compartment is where the dilution indicator mixes with blood at a high rate. The water mass and blood mass constituted the state for each compartment. The following criteria may be used:

Ultrafiltration removes fluid from the central compartment at the prescribed rate $q_{ufr}$.

The indicator fluid or liquid is injected into the central compartment at a rate of $q_{ind}$. Instantaneous mixing may be assumed within each compartment. Following the injection, the indicator fluid may be assumed to arrive at the measurement site with a fixed time delay after circulating throughout the body.

Over the time period of interest (e.g., 20 min), both $q_1(t)/V_1(t)$ and $q_2(t)/V_2(t)$ may be taken as constants. Here $q_1$ is the blood flow from the central to peripheral compartments, $q_2$ is the blood flow from peripheral to central compartments, and $V_1$ and $V_2$ are the fluid volumes for the central and peripheral compartments, respectively.

The fluid exchange between the interstitial and intravascular spaces, referred to as refilling/filtration, may occur between the interstitial and peripheral compartments. For simplicity, this nonlinear exchange $q_f$ may be taken as an affine function of the central volume as in Eq. 1:

$$q_f = q_{f0} + \alpha V.  \qquad \text{Eq. 1}$$

In an example, $q_f$ depends only on the central volume since the interstitial volume may be much larger than the volume of fluid removed by ultrafiltration within the time period. The coefficient $\alpha$ models the sensitivity of $q_f$ to the lymphatic flow rate and the nonlinear Starling mechanism describing microvascular refilling/filtration flow into the peripheral compartment.

The water content $W_{ind}$ and density of dilution $\rho_{ind}$ may be around 0.991 kg/kg and 1.0 kg/L, respectively. The water content and density as the diluted indicator (e.g., ultra-pure dialysate) may be the same for the fluid removed from intravascular space by ultrafiltration (denoted by $W_{ufr}$ and $\rho_{ufr}$) and filtration (denoted by $W_f$ and $\rho_f$).

The mass balance equations for the indicator fluid (water) and blood in each compartment in the model are described below.

Central Compartment:
Indicator Mass Balance:

$$\frac{dm_{w,1}(t)}{dt} = -\frac{q_1(t)}{V_1(t)}m_{w,1} + \frac{q_2(t)}{V_2(t)}m_{w,2} + W_{ind}\rho_{ind}q_{ind}(t) - W_{ufr}\rho_{ufr}q_{ufr}(t), \qquad \text{Eq. 2}$$

Blood Mass Balance:

$$\frac{d}{dt}(\rho_1 V_1) = -\rho_1 q_1(t) + \rho_2 q_2(t) + \rho_{ind}q_{ind}(t) - \rho_{ufr}q_{ufr}(t). \qquad \text{Eq. 3}$$

Peripheral Compartment:
Indicator Mass Balance:

$$\frac{dm_{w,2}(t)}{dt} = \frac{q_1(t)}{V_1(t)}m_{w,1} - \frac{q_2(t)}{V_2(t)}m_{w,2} + W_f \rho_f q_f(t), \qquad \text{Eq. 4}$$

Blood Mass Balance:

$$\frac{d}{dt}(\rho_2 V_2) = \rho_1 q_1(t) - \rho_2 q_2(t) + \rho_f q_f(t). \qquad \text{Eq. 5}$$

where $m_{w,i}$ denotes water mass, $V_i$ denotes fluid volume, $W_i=m_{w,i}/\rho_i V_i$ is the water content, $\rho_i$ is fluid density calculated from $W_i$ and temperature as described elsewhere. Blood mass and water mass define the state for each compartment. Subscript i=1,2 denotes central compartment and peripheral compartment, respectively, and subscripts ufr and ind denote ultrafiltration and indicator dilution, respectively. For example, $W_{ind}$ denotes the water content of the indicator injection and $W_{ufr}$ is the water content of fluid removed by ultrafiltration. In the above equations, $W_{ind}$ $\rho_{ind}$ $q_{ind}$ and $W_f\rho_f q_f$ equal the rate of water mass added by indicator dilution and refilling/filtration, respectively, and $W_{ufr}$ $\rho_{ufr}$ $q_{ufr}$ is the rate of water mass removed by ultrafiltration.

$$\frac{q_2(t)}{V_2(t)}m_{w,2} \text{ and } \frac{q_1(t)}{V_1(t)}m_{w,1}$$

denote the convective inflow between compartments. Other terms can be interpreted in a similar manner.

As the blood volume monitor (BVM) may not be available in certain locations, an optical sensor for measuring hematocrit level during hemodialysis, such as a CritLine sensor (manufactured by Fresenius Medical Care, Waltham, MA) integrated into dialysis machines may be used. However, rather than providing blood water content (or total protein concentration) as in the BVM, the CritLine provides hematocrit data. Other sensors that produce similar tangible data such as BWC or hematocrit data may be used. Given the comparability of RBV measurements obtained by BVM and CritLine measurements, assessed using published methods, the variable-volume two-compartment model for blood water content developed for the BVM is easily converted into a model suitable for CritLine data. This is done using the relation: EWC*H+PWC*(1−H)=BWC, where PWC (plasma water content) is 0.93 and EWC (erythrocyte water content) is 0.72, and H is hematocrit.

The output is the measured water content defined as water mass over blood mass. In the technique described herein, water content of blood W may be measured in the arterial line of extracorporeal circulation. Subscript m refers to the measurement. In AV patients, arterial blood from the fistula/graft enters the extracorporeal circulation with high flow rate before equilibrating with the peripheral compartment because of so-called cardio-pulmonary recirculation. $W_m$ measures the central compartment's water content ($W_m=W_1=m_{w,1}/\rho_1 V_1$). For CV patients, venous blood from the superior vena cava, a mix of blood from both compartments, enters the extracorporeal circulation. Therefore, $W_m$ comprises an almost half- and half mix of water contents from each compartment ($W_m=0.5$ $[W_1+W_2]=0.5$ $[m_{w,1}/\rho_1 V_1+m_{w,2}/\rho_2 V_2]$). The variation in blood water content due to indicator dilution appears at the measurement site with a time delay after circulating the body, and may be modeled using a Heaviside function, $H(t-t_{delay})$.

The feasibility of obtaining reasonable estimates depends on several factors including model structure and model complexity relative to what is measured. A dynamic system is said to be observable if the initial states can be determined from system's measured outputs. Observability is a necessary condition for parameter identification, but is not a sufficient condition for identifiability. An analysis based on linearization shows that the two-compartment model described by Eqs. 2-5 may become unobservable when the output measures mixed venous blood water content sampled from a central venous access.

Parameters of the two-compartment model (as shown in schematic diagram 100) for CV patients are not identifiable because the measurement $W_m$ is an unknown function of $W_1=m_{w,1}/\rho_1 V_1$ and $W_2=m_{w,2}/\rho_2 V_2$. To overcome this limitation, the states of central compartment and peripheral compartment may be taken as equal to each other (i.e. $m_{w,1}=m_{w,2}$ and $\rho_1 V_1=\rho_2 V_2$.). Using this assumption, the mass balance equations for the central and peripheral compartments can be combined to define a new set of mass balance equations consisting of two equations that include the both compartments. In other words, this assumption transforms the unobservable two-compartment model into an observable, single-compartment model. This assumption is supported by the fact that the post-dilution slope of the measured BWC in CV patients depicts a single exponential decay suggesting an observable single compartment behavior. A list of model estimated parameters is given in Table 1 below.

TABLE 1

| Parameters to be estimated Parameter (units) | |
| --- | --- |
| Central Compartment's volume at start of analysis (L) | $V_1(t_0)$ |
| Peripheral Compartment's volume at start of analysis (L) | $V_2(t_0)$ |
| Blood exchange between compartments (L/min) | $q_1(t_0)$ |
| Fluid exchange with interstitial space (L/min and L/min$^2$) | $q_{f0}$ and $\alpha$ |
| Time delay (min) | $t_{delay}$ |

In an example, the parameter estimation is conducted using a nonlinear least squares, such as with the "trust-region-reflective" algorithm in MATLAB, in which the parameters are identified to minimize the root-mean-square error (RMSE) between the water content measurements $W_m$ and the water content estimates $W_{estimates}$ obtained by the technique described herein. The RMSE may be defined as:

$$\text{RMS}E = \sqrt{\frac{\sum_{k=1}^{N}(W_{estimates}-W_m)}{N}}. \qquad \text{Eq. 6}$$

Parameter estimation may be conducted 5 minutes prior to and 10 minutes after indicator injection time, by taking samples of $W_m$ over the 15 minute time period.

Figure 2A:
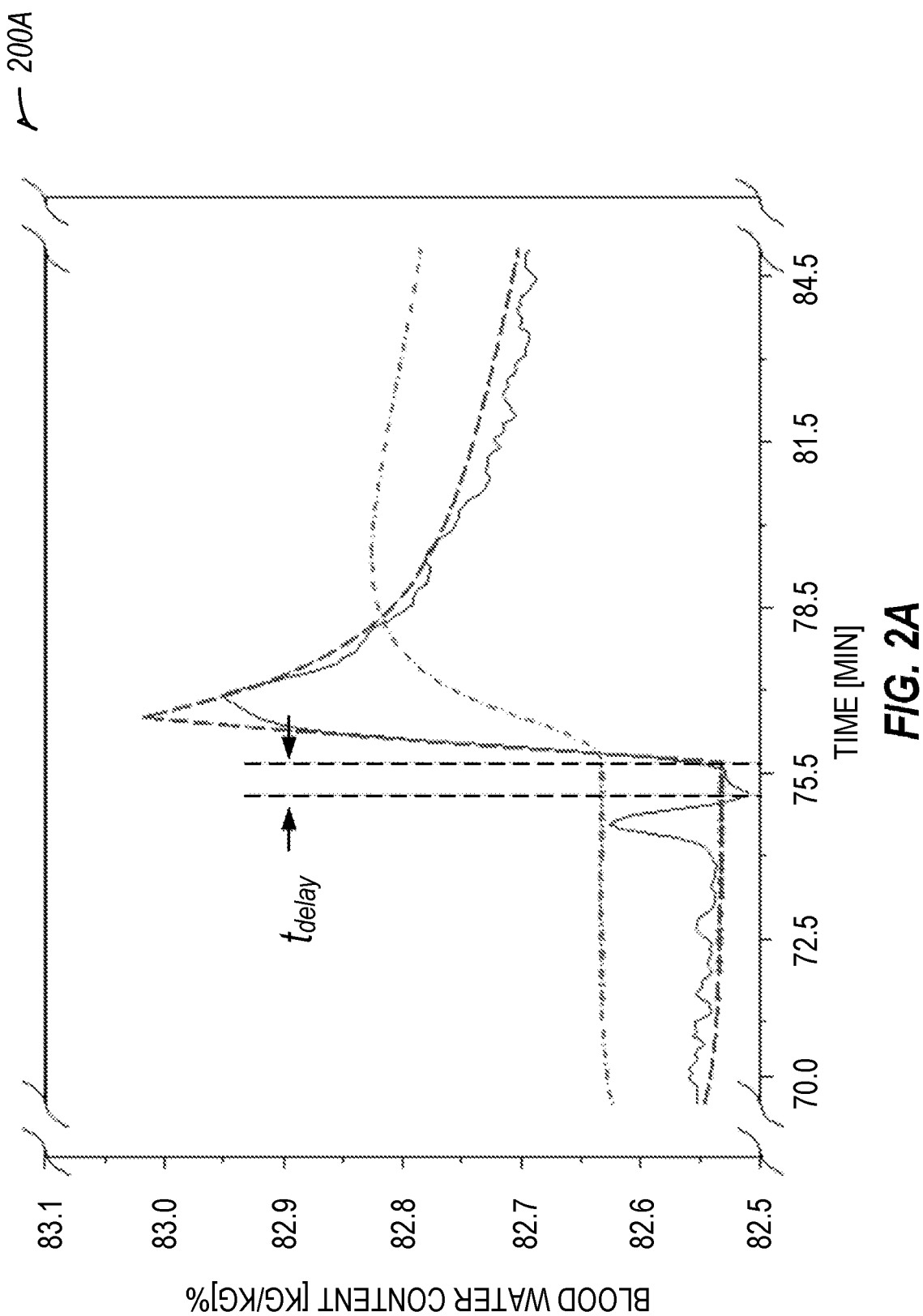
FIGS. 2A-2B illustrate graphs showing parameter estimation details for a patient in accordance with some embodiments.
Figure 2B:
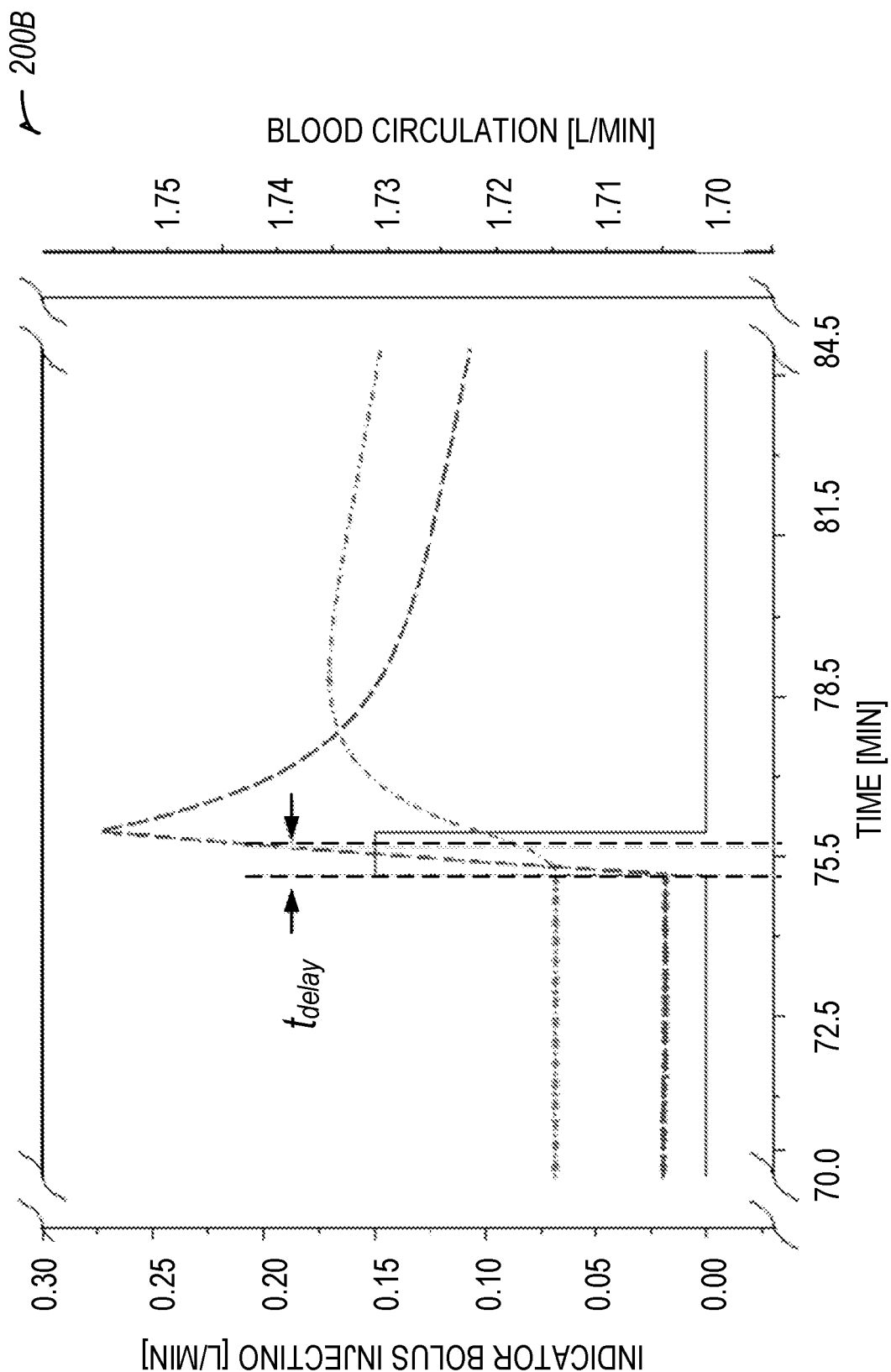

FIGS. 2A-2B illustrate graphs 200A and 200B showing parameter estimation details for a patient in accordance with some embodiments. For example, graphs 200A and 200B show estimation details for a patient at a first injection (e.g., RMSE=0.02 kg/kg). Graph 200A includes estimated blood water content of a central compartment (represented by a dashed line), a peripheral compartment (represented by a dashed-dot line) and a measurement (represented by a solid line). The variation in blood water content due to the indicator dilution shows up at measurement site with a time delay, $t_{delay}$. Graph 200B includes an administered indicator dilution profile (represented by a solid line), and inter-compartment flows $q_1(t)$ (represented by a dashed line) and $q_2(t)$ (represented by a dashed-dot line).

FIGS. 2A-2B summarize estimation results for an AV patient. Graph 200A shows the variation of BWC in each compartment throughout the indicator dilution protocol and graph 200B shows the variation in flow rates between compartments within the dilution protocol. The spike in the measured variation of BWC occurring at t=74 min is due to automatic transmembrane pressure tests (TMP) from the dialysis machine. These spikes are repeated every 15 min and each spike affects measurements for about 3 min. Since dilution starts immediately after these TMP tests, a 5 min period prior to dilution ensures that 2 min of spike-free data may be collected prior to dilution. Since the two-compartment model equilibrated after an injection in about 10 min, a 15 min sampling period may be used as a good compromise between practicality and the model's approximation of the actual nonlinear and time-varying phenomena.

The estimate of ABV at any time of interest V(t) is derived from the sum of the two estimated compartments (central and peripheral $V(t_0)=V_1(t_0)+V_2(t_0)$) at time of start of dilution to and measured relative blood volume (RBV(t), vol/vol) at injection time and at time of interest:

$$\frac{RBV(t_0)}{RBV(t)} = \frac{V(t_0)}{V(t)}. \quad \text{Eq. 7}$$

In an example, at the start of the dialysis treatment RBV(0)=1.

The differences between the techniques (the VVKM technique described herein versus the BEXP) may be assessed using a two-sided 95% statistical tolerance interval (TI) (confidence level 95%) for a population of differences having a normal distribution with unknown variability. Nested one-way analysis of variance (ANOVA) may be used to compute and compare the intratreatment variability of estimates in the two techniques. Patients may be chosen as the main factor while treatments (within patients) may be taken as the nested factor. Normally distributed results include using mean and standard deviation (SD), or median (e.g., first quartile-third quartile). In an example, a Shapiro-Wilk test may be used to test normality.

Figure 3A:
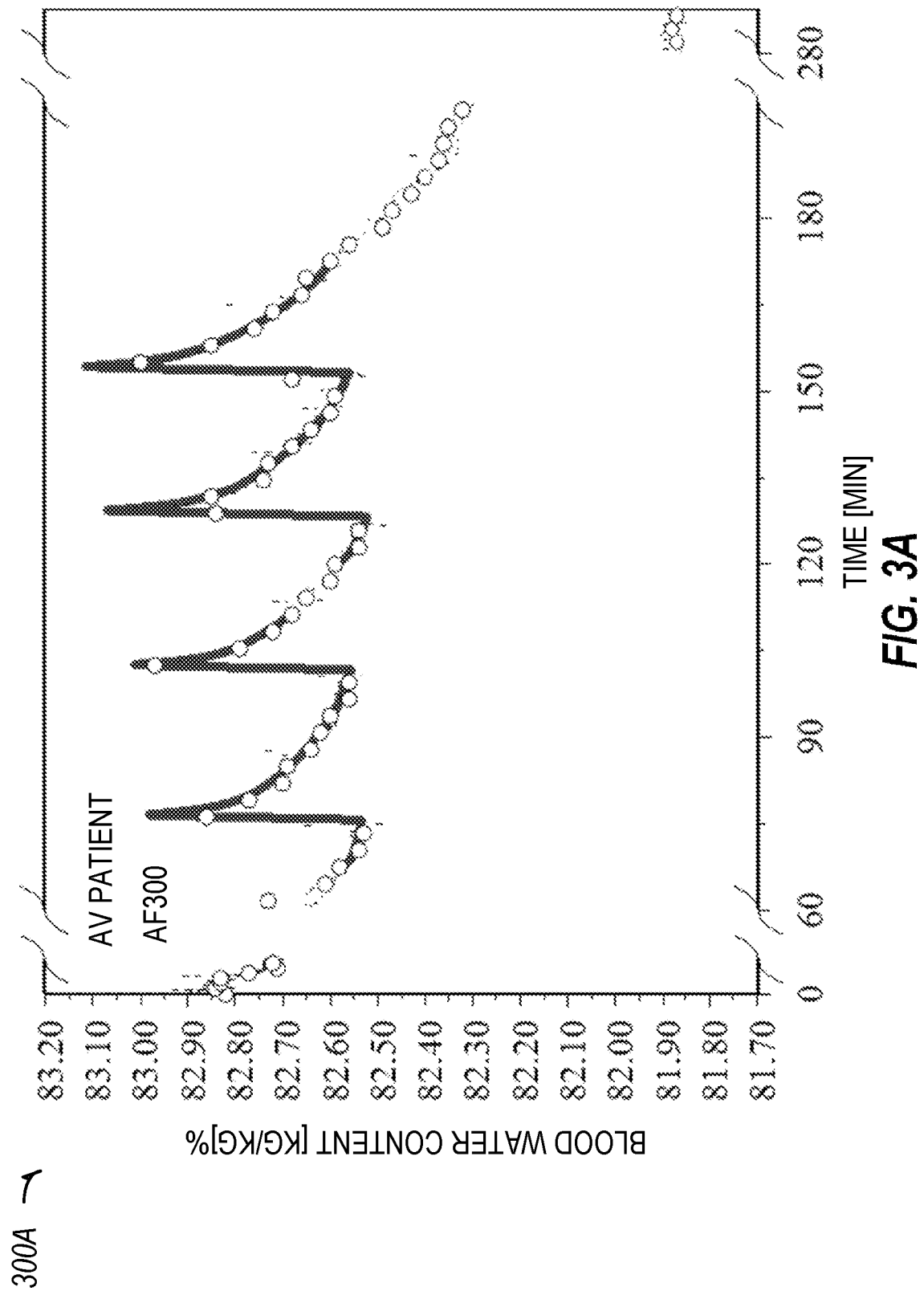
FIGS. 3A-3B illustrate graphs showing an overview of measured water content and parameter estimation in accordance with some embodiments.
Figure 3B:
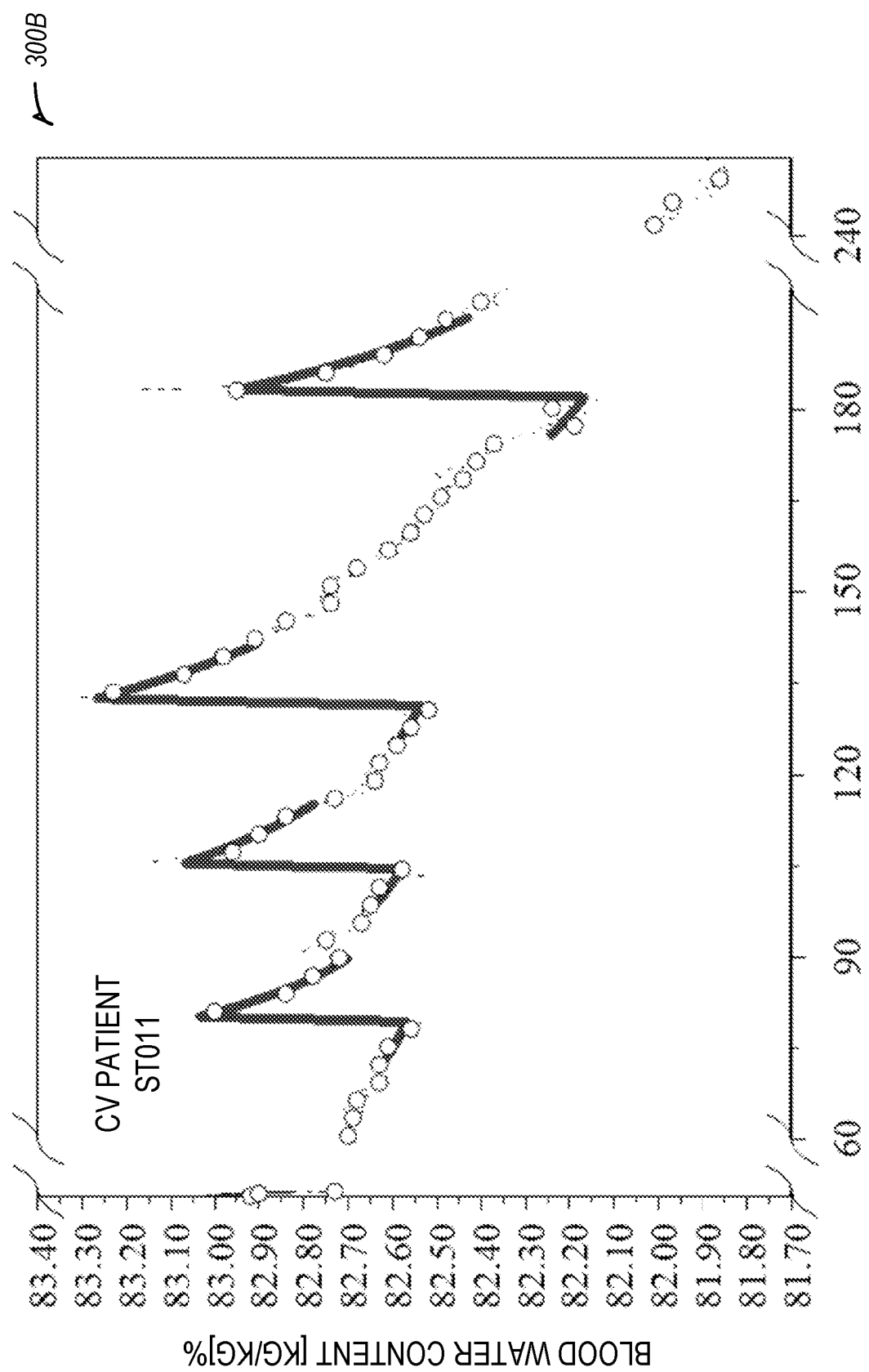

FIGS. 3A-3B illustrate graphs 300A and 300B showing an overview of measured water content and parameter estimation in accordance with some embodiments. Graphs 300A and 300B illustrate an overview of measured water content (represented by a dashed line with a circle symbol) and a model estimation (represented by a solid line) during dialysis session for an arterio-venous (AV) access patient (graph 300A) and a central-venous (CV) access patient (graph 300B).

In an example, 85 bolus dilution tests (60 to 210 mL) of ultrapure dialysate were performed over 21 dialysis treatments in 6 patients using multiple indicator dilutions within each treatment. The descriptive statistics of the estimation results are given in Table 2 below.

TABLE 2

Descriptive statistics of estimates*
Variable* (unit)

| | |
|---|---|
| Central compartment blood volume at $t = 0$, $V_1(0)^{**}$ (L) | 2.83 (0.66) |
| Peripheral compartment blood volume at $t = 0$, $V_2(0)^{**}$ (L) | 2.98 (0.66) |
| Intravascular blood volume at $t = 0$, $V(0)^{***}$ (L) | 4.16 [3.80-5.59] |
| Specific blood volume (kg/mL) | 71.94 [51.40-79.97] |
| Blood exchange between compartments, $q_1(t_0)$ (L/min) | 1.64 (0.39) |

TABLE 2-continued

Descriptive statistics of estimates*
Variable* (unit)

| | |
|---|---|
| Fluid exchange with interstitial space, $q_{f0}$ (mL/min) | 10.26 (5.62) |
| Fluid exchange with interstitial space, $\alpha$ (mL/min$^2$) | 21.12 (21.94) |
| Time delay, $t_{delay}$ (min) | 0.68 [0.56-0.84] |
| RMSE (kg/kg) | 0.02 [0.02-0.03] |

*Normal distributed results are reported using mean(SD), otherwise, median [first quartile-third quartile]. Shapiro-Wilk test is used to test normality.
**only includes AV patient results as the parameter is not available (identifiable) in CV patient.
***includes both AV and CV patient results FIGS. 3A-3B show measured water content and the estimation using the VVKM technique for an AV patient (graph 300A) and a CV patient (graph 300B). The estimated BWC was accurate compared to the measured BWC, with RMSE less than 0.02 kg/kg (2%) and 0.03 kg/kg (3%) for AV and CV patients, respectively.

A normal probability plot (not shown) and a Shapiro-Wilk test for AV patients indicated that the differences between the ABV estimates of the BEXP and VVKM techniques were normally distributed with mean of 0.02 L, standard deviation (SD) of 0.52 L, and with a 95% tolerance interval from 1.27 L to 1.32 L. For CV patients, the differences were also normally distributed with mean of 0.09 L, SD of 0.42 L, and with 95% tolerance interval from 1.10 L to 0.91 L. Thus, the systematic difference between the VVKM and the BEXP techniques was negligible.

Figure 4:
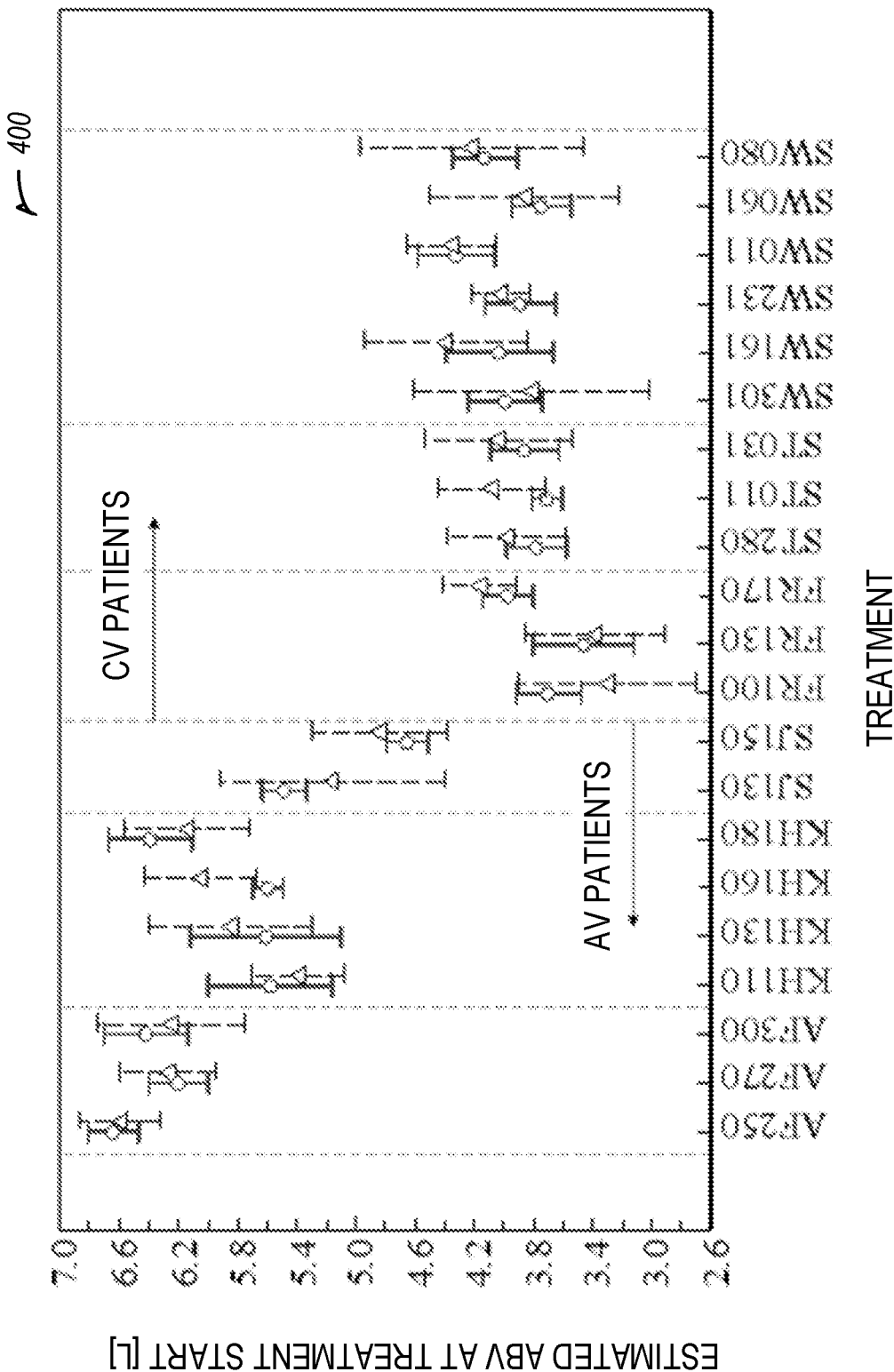
FIG. 4 illustrates a graph showing comparative intratreatment variability of absolute blood volume (ABV) estimates for two techniques in accordance with some embodiments.

FIG. 4 illustrates a graph 400 showing comparative intratreatment variability of absolute blood volume (ABV) estimates for two techniques in accordance with some embodiments. Graph 400 illustrates intratreatment variability of ABV estimates (mean+/−SD) in arterio-venous (AV) and central-venous (CV) access patients. The physiologically motivated kinetic model for the VVKM technique (represented by a line with the circle for mean) is compared in graph 400 to a classic mono back-extrapolation method BEXP technique (represented by a dashed line with triangle for mean).

Since a patient may have different blood volumes on different treatment days, the VVKM technique described herein may change for a patient at different times (e.g., from morning to afternoon, or different days). The VVKM technique was compared to the BEXP technique at similar times in order to provide an accurate comparison. FIG. 4 provides such a comparison. Within each treatment, three to five indicator dilutions were administered. The ABV estimates at the start of dialysis treatment obtained from dilutions within the same treatment are summarized as mean+/−SD. Results showed that the VVKM technique has improved reproducibility by virtue of lower SD in all 11 treatments in CV patients, and in 8 out of 9 instances in AV patients compared to the BEXP technique. Thus, the VVKM technique is more accurate than the BEXP technique.

The results of nested one-way analysis of variance are presented in Table 3 below.

TABLE 3

Nested one-way ANOVA of absolute blood volume

| | | | Intravascular blood water content kinetic model (VVKM) (L) | | | Back-extrapolation algorithm (BEXP) algorithm (L) | | |
|---|---|---|---|---|---|---|---|---|
| | | Deg. of freedom | Sum of Sqs. | Mean square | Standard dev | Sum of Sqs. | Mean square | Standard dev |
| Arterio-venous (AV) access Patients | Inter-patient | 2 | 8.81 | 4.41 | 2.08 | 9.07 | 4.53 | 2.13 |
| | Inter-treatment | 6 | 3.29 | 0.55 | 0.73 | 1.84 | 0.31 | 0.54 |
| | Intra-treatment | 26 | 1.80 | 0.07 | 0.27 | 5.10 | 0.22 | 0.47 |

TABLE 3-continued

Nested one-way ANOVA of absolute blood volume

| | | Deg. of freedom | Intravascular blood water content kinetic model (VVKM) (L) | | | Back-extrapolation algorithm (BEXP) algorithm (L) | | |
|---|---|---|---|---|---|---|---|---|
| | | | Sum of Sqs. | Mean square | Standard dev | Sum of Sqs. | Mean square | Standard dev |
| central-venous (CV) access patients | Inter-patient | 2 | 0.95 | 0.48 | 0.69 | 2.07 | 1.04 | 1.01 |
| | Inter-treatment | 9 | 1.40 | 0.15 | 0.39 | 3.17 | 0.35 | 0.59 |
| | Intra-treatment | 39 | 2.33 | 0.06 | 0.24 | 10.31 | 0.26 | 0.51 |

Intratreatment SDs for the BEXP estimates were 0.51 L and 0.47 L for CV and AV patients respectively; and the corresponding SDs for VVKM estimates were 0.24 L and 0.27 L for CV and AV patients, indicating significant reductions in variability by 53% and 42% respectively. The AV and CV intratreatment coefficients of variation were 0.080 and 0.128 for BEXP, and 0.046 and 0.062 for VVKM.

Figure 5:
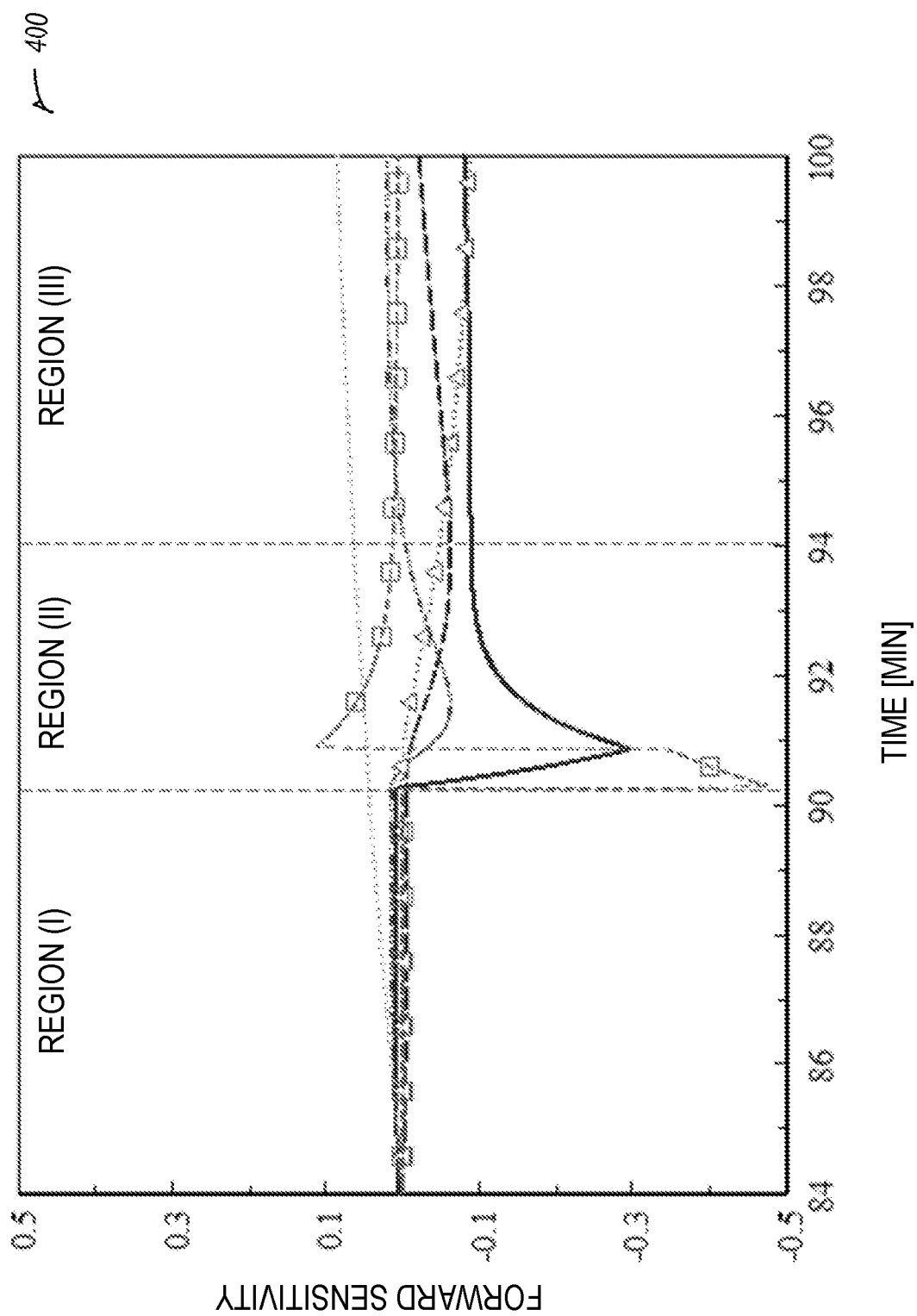
FIG. 5 illustrates a graph showing a forward sensitivity analysis for estimated parameters in accordance with some embodiments.

FIG. 5 illustrates a graph 500 showing a forward sensitivity analysis for estimated parameters in accordance with some embodiments. The forward sensitivity analysis includes five model parameters for an arterio-venous (AV) access patient at first dilution experiment before (Region I), during (Region II), and after the perturbation (Region III). The five model parameters include a central compartment volume $V_1(t_0)$ (represented by a solid line), a peripheral compartment volume $V_1(t_0)$ (represented by a dashed line), a blood exchange between compartments $q_1(0)$ (represented by a dashed-dotted line), a refilling/filtration $q_f(0)$ and $\alpha$ (represented by a triangle, dotted line), a time delay $t_{delay}$ (represented by a rectangle, dashed line).

ABV during a dialysis treatment may be successfully estimated using an indicator dilution protocol and the physiologically-motivated compartmental model (VVKM). The dilution protocol delivers boluses of ultra-pure dialysate using the bolus function of a modern dialysis machine. When compared to other solutions such as normal saline, this ultra-pure dialysate has the advantage of being readily available at the proper temperature and osmotic concentration. In an example, the VVKM technique may be extended for hemoglobin and hematocrit measurements available within almost all dialysis machines.

The fidelity of the parameter estimation technique may be verified by analyzing the sensitivity of the model's output to changes in the model parameters. For example, forward sensitivity analysis (FSA) may be used to compare sensitivities at each sampled point in time. In an example, the forward sensitivity function may be multiplied by the model parameter to define an unnormalized forward sensitivity function with respect to a parameter in cases where the magnitudes of the parameters differ considerably. The unnormalized forward sensitivity function with respect to a model parameter $p_i$ is given by:

$$S_i = p_i \frac{\partial W_m}{\partial p_i}(t, p),\quad\text{Eq. 8}$$

where p is the vector of model parameters $p_i$. FIG. 5 shows an example of this sensitivity analysis for an AV patient. The plot is divided into three regions: region I captures dynamics prior to dilution, region II captures dynamics immediately after dilution which is dominated by mixing between compartments, and region III captures post-mixing dynamics referred to as the elimination phase, for example starting 4 min after dilution. FIG. 5 shows that the model output Wm has much lower sensitivity to model parameters in region I compared to the other regions. The output is dominated by refilling/filtration prior to dilution in region I, by time delay and compartmental volumes during mixing in region II, and by central compartment volume and refilling/filtration during the elimination phase (region III). The output is most sensitive to the central compartment's volume in region II with sensitivity dropping significantly in region III. The shape of the curves of FIG. 5 become similar to each other moving from region II to region III. Since the BEXP algorithm is limited to modelling only the elimination phase (region III), it is less likely to uniquely identify parameters.

FIG. 5 shows that the VVKM technique has a higher sensitivity for estimates of central compartment volume $V_1(t_0)$ compared to peripheral compartment volume $V_2(t_0)$, and lower sensitivities for other model parameters such as blood exchange between compartments. Sensitivity analysis indicates higher variabilities in the estimates of these parameters which is consistent with actual estimation results. Separate sensitivity analysis using a modified model which has ABV as a state indicates good $ABV(t_0)$ sensitivity. For example, for AV patients, intratreatment SD of estimates for $V_1(t_0)$ and $V_2(t_0)$ is 0.23 L and 0.32 L, while the SD of $ABV(t_0)=V_1(t_0)+V_2(t_0)$ is only 0.27 L.

The forward sensitivity function is a function of time that indicates the sensitivity of the model's output at any time to changes in the parameters. Therefore, it indirectly indicates how to select sample points in time to enhance information provided by the measurement, as more information can be extracted from a sample point with high sensitivity. This becomes useful when only a limited number of measurements can be recorded. ABV estimates in an example include added extracorporeal circulation volume, estimated to be around 300±10 mL. In this example, this volume is subtracted from the VVKM technique estimates to obtain actual absolute blood volume.

Figure 6:
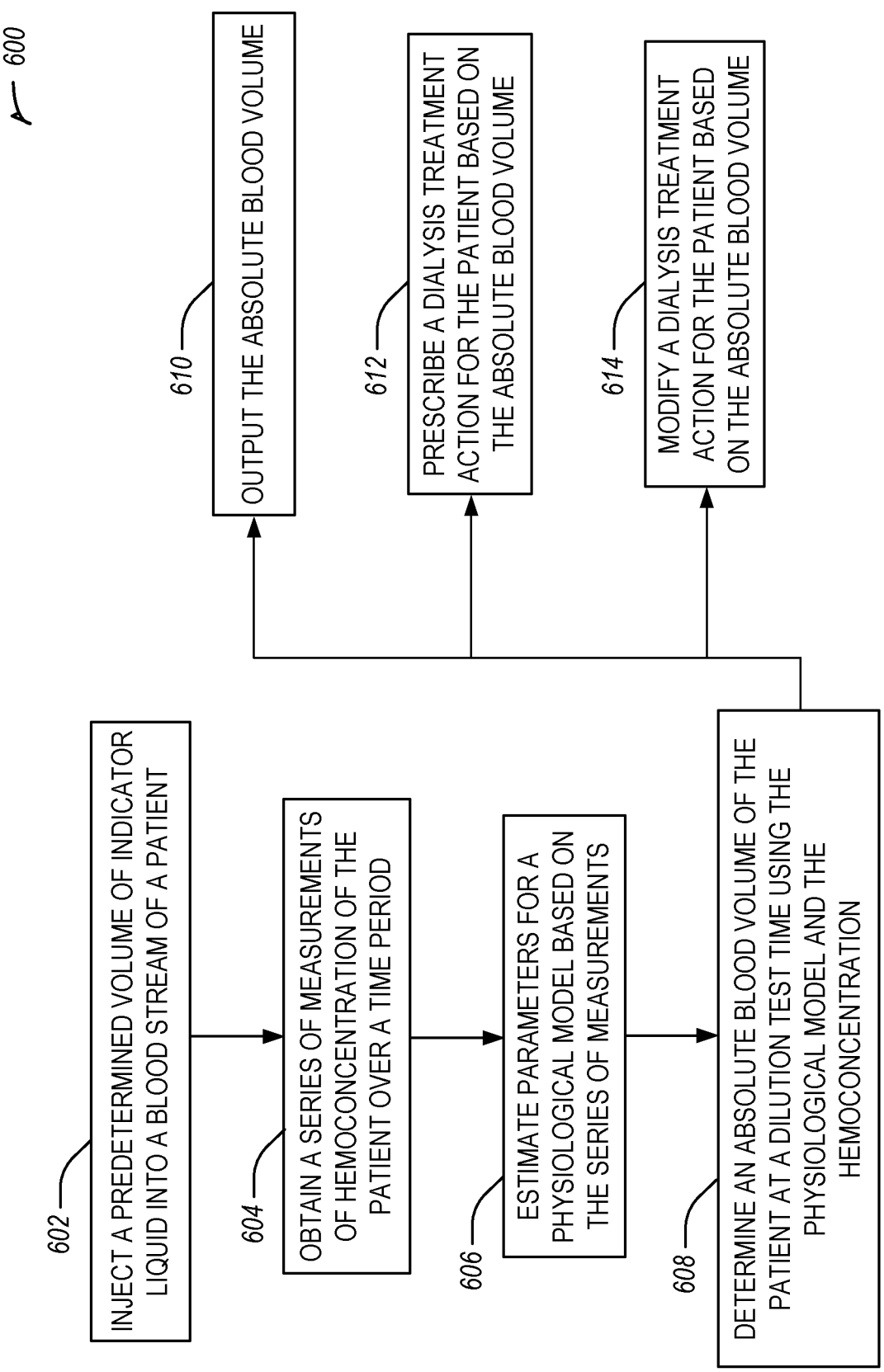
FIG. 6 illustrates a flow chart showing a technique for estimating absolute blood volume (ABV) in accordance with some embodiments.

FIG. 6 illustrates a flow chart showing a technique 600 for estimating ABV in accordance with some embodiments. The technique 600 may be stored using at least one non-transitory machine-readable medium. The machine-readable medium may include instructions, which when executed by at least one processor or a machine, cause the at least one processor or the machine to perform the technique 600. The technique 600 includes an operation 602 to inject a predetermined volume of liquid (e.g., indicator or dilution indicator liquid) into a blood stream of a patient. The liquid may be injected using a pump or an injector. In an example, the pump may be included in a dialysis machine, such as a hemodialysis, hemodiafiltration, or the like. In another example, the pump may be an external pump to a dialysis machine. The pump (external or internal to a dialysis machine) may be used to connect to a patient's blood such that blood can be taken outside of the body and cleaned, such as with water removed. The liquid may include saline.

The technique 600 includes an operation 604 to obtain a series of measurements of hemoconcentration of at least one blood characteristic, such as relative blood volume, BVM, or hematocrit data (e.g., from a hematocrit sensor) of the patient over a time period. In an example, the series of measurements may be taken before the injection in operation 602. These measurements may be in addition to measurements taken after the injection. The series of measurements may include a hemoconcentration, a relative blood volume, BVM, or hematocrit data from a hematocrit sensor at a dilution test time during the time period. The series of measurements of hemoconcentration may be based on a comparison of blood volume to the predetermined volume of liquid. In an example, the dilution test time may be at a discrete time or over a period, such as at or during ten to fifteen minutes after the dilution injection time, where the injection occurs at the dilution injection time. The time period may include a period before the dilution injection time, such as five minutes prior at an initial time or start of hemodialysis. In an example, the series of measurements may include measurements taken during the period before the dilution injection time for a baseline.

The technique 600 includes an operation 606 to estimate parameters for a physiological model based on the series of measurements. The parameters may include the hemoconcentration at the dilution test time, a volume of a first compartment at a dilution injection time, such as at a start of the time period (e.g., five minutes after an initial time or a start time of hemodialysis, or the time of injection of the dilution), or a volume of a second compartment at the dilution injection time. In an example, the estimated parameters may be unique to the patient at the dilution injection time. For example, the estimated parameters may be patient-specific or may change over time. In an example, the estimated parameters include a blood exchange between the first and second compartments, a fluid exchange with interstitial space, or a time delay. In an example, estimating the parameters may include fitting the physiological model to the series of measurements. This example may further include performing a nonlinear least squares fit or minimizing a root-mean-square error between the series of measurements and relative blood volume estimates resulting from the physiological model. In an example, estimating the parameters may include using a patient-specific attribute, such as gender, age, weight, comorbidity, etc. The operation 606 may include estimating parameters at the dilution test time.

The technique 600 includes an operation 608 to determine an absolute blood volume of the patient at the dilution test time using the physiological model and the hemoconcentration at the dilution test. Operation 608 may include using a relative blood volume, BVM, or hematocrit, such as using a hematocrit sensor (e.g., Crit-Line) at the dilution injection time. In response to determining the ABV, the technique 600 may include one or more of operations 610, 612, or 614. Operation 610 includes outputting the ABV. Operation 612 includes prescribing a dialysis treatment action for the patient based on the ABV. Operation 614 includes modifying a dialysis treatment action for the patient based on the ABV.

In an example, operations 612 or 614 may include changing an amount of fluid removed by ultrafiltration or changing the ultrafiltration profile, or extending the dialysis treatment time, or modifying the dry weight of the patient, or introducing temperature and/or dialysate sodium profiles, such as to prevent intradialytic hypotension when too much fluid is removed or to prevent edema, left ventricular hypertrophy, or heart failure, when too little fluid is removed. In an example, operations 612 or 614 may include using the ABV to determine a fluid balance within a dialysis treatment and return the patient to a dry weight, thereby improving dialysis outcomes.

Example 1 is a dialysis machine for estimating absolute blood volume, the dialysis machine comprising: an injector to inject a predetermined volume of dilution indicator liquid into a blood stream of a patient; a receiver to obtain, from a sensor, a series of measurements of hemoconcentration of at least one blood characteristic of the patient over a time period, the series of measurements including a hemoconcentration at a dilution test time during the time period, and the series of measurements of hemoconcentration based on blood volume compared to the predetermined volume of dilution indicator liquid; memory including instructions, which when executed by a processor, cause the processor to: estimate parameters for a physiological model based on the series of measurements, the parameters including the hemoconcentration at the dilution test time, a volume of a first compartment and a volume of a second compartment at the dilution test time and at a dilution injection time of the time period; and determine an absolute blood volume of the patient at the specified time using the physiological model and the series of measurements of hemoconcentration; and a display portion to display the absolute blood volume.

In Example 2, the subject matter of Example 1 includes, wherein the memory includes instructions to further cause the processor to prescribe a dialysis treatment action for the patient based on the absolute blood volume at the dilution test time.

In Example 3, the subject matter of Examples 1-2 includes, wherein the memory includes instructions to further cause the processor to modify a dialysis treatment action for the patient automatically based on the absolute blood volume.

In Example 4, the subject matter of Examples 1-3 includes, wherein the dilution test time includes a period of ten to fifteen minutes after the dilution injection time, and wherein the injection occurs at the dilution injection time.

In Example 5, the subject matter of Examples 1-4 includes, wherein the time period includes a period before the dilution injection time and the series of measurements include measurements taken during the period before the dilution injection time for a baseline.

In Example 6, the subject matter of Examples 1-5 includes, wherein the estimated parameters include a blood exchange between the first and second compartments, a fluid exchange with interstitial space, and a time delay.

In Example 7, the subject matter of Examples 1-6 includes, wherein estimating the parameters includes fitting the physiological model to the series of measurements by performing a nonlinear least squares fit and minimizing a root-mean-square error between the series of measurements and relative blood volume estimates resulting from the physiological model.

In Example 8, the subject matter of Examples 1-7 includes, wherein the series of measurements of hemoconcentration include a series of measurements of at least one of a relative blood volume, a blood volume monitor (BVM) measurement, or a hematocrit measurement.

Example 9 is a method for estimating absolute blood volume, the method comprising: injecting, using a pump, a predetermined volume of indicator liquid into a blood stream of a patient; obtaining, via a sensor, a series of measurements of hemoconcentration of at least one blood characteristic of the patient over a time period, the series of measurements including a hemoconcentration at a dilution test time during the time period, and the series of measurements of hemoconcentration based on blood volume compared to the predetermined volume of indicator liquid; estimating parameters for a physiological model based on the series of measurements, the parameters including the hemoconcentration at the dilution test time, a volume of a first compartment and a volume of a second compartment at the dilution test time and at an dilution injection time of the time period; determining an absolute blood volume of the patient at the dilution test time using the physiological model and the series of measurements of hemoconcentration; and outputting the absolute blood volume on a display portion of the dialysis machine.

In Example 10, the subject matter of Example 9 includes, prescribing, at the dialysis machine, a dialysis treatment action for the patient based on the absolute blood volume at the dilution test time.

In Example 11, the subject matter of Examples 9-10 includes, modifying, at the dialysis machine, a dialysis treatment action for the patient automatically based on the absolute blood volume.

In Example 12, the subject matter of Examples 9-11 includes, wherein the dilution test time is ten minutes after the dilution injection time, and wherein the injection occurs at the dilution injection time.

In Example 13, the subject matter of Examples 9-12 includes, wherein the time period includes a period before the dilution injection time and the series of measurements include measurements taken during the period before the dilution injection time for a baseline.

In Example 14, the subject matter of Examples 9-13 includes, wherein the estimated parameters are unique to the patient at the dilution injection time.

In Example 15, the subject matter of Examples 9-14 includes, wherein the estimated parameters include a blood exchange between the first and second compartments, a fluid exchange with interstitial space, and a time delay.

In Example 16, the subject matter of Examples 9-15 includes, wherein estimating the parameters includes fitting the physiological model to the series of measurements.

In Example 17, the subject matter of Example 16 includes, wherein fitting the physiological model to the series of measurements includes performing a nonlinear least squares fit and minimizing a root-mean-square error between the series of measurements and blood volume estimates resulting from the physiological model.

In Example 18, the subject matter of Examples 9-17 includes, wherein estimating the parameters may include using a patient-specific attribute including gender, age, weight, ethnicity, or comorbidity.

In Example 19, the subject matter of Examples 9-18 includes, wherein the at least one blood characteristic includes at least one of a relative blood volume, a blood volume monitor (BVM) measurement, a hematocrit measurement, or a hemoconcentration measurement.

Example 20 is at least one non-transitory machine-readable medium including instructions, which when executed by at least one processor, cause the at least one processor to perform operations of any of the methods of Examples 9-19.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method for estimating absolute blood volume at a dialysis machine, the method comprising:
   injecting, using a pump, a predetermined volume of indicator liquid into a blood stream of a patient;
   obtaining, via a sensor, a series of measurements of hemoconcentration of at least one blood characteristic of the patient over a time period, the series of measurements including a hemoconcentration at a dilution test time during the time period, and the series of measurements of hemoconcentration based on blood volume compared to the predetermined volume of indicator liquid;
   estimating parameters for a physiological model based on the series of measurements, the parameters including the hemoconcentration at the dilution test time, a volume of a first compartment and a volume of a second compartment at the dilution test time and at an dilution injection time of the time period;
   determining an absolute blood volume of the patient at the dilution test time using the physiological model and the series of measurements of hemoconcentration; and
   outputting the absolute blood volume on a display portion of the dialysis machine.

2. The method of claim 1, further comprising, prescribing, at the dialysis machine, a dialysis treatment action for the patient based on the absolute blood volume at the dilution test time.

3. The method of claim 1, further comprising, modifying, at the dialysis machine, a dialysis treatment action for the patient automatically based on the absolute blood volume.

4. The method of claim 1, wherein the dilution test time is ten minutes after the dilution injection time, and wherein the injection occurs at the dilution injection time.

5. The method of claim 1, wherein the time period includes a period before the dilution injection time and the series of measurements include measurements taken during the period before the dilution injection time for a baseline.

6. The method of claim 1, wherein the estimated parameters are unique to the patient at the dilution injection time.

7. The method of claim 1, wherein the estimated parameters include a blood exchange between the first and second compartments, a fluid exchange with interstitial space, and a time delay.

8. The method of claim 1, wherein estimating the parameters includes fitting the physiological model to the series of measurements.

9. The method of claim 8, wherein fitting the physiological model to the series of measurements includes performing a nonlinear least squares fit and minimizing a root-mean-square error between the series of measurements and blood volume estimates resulting from the physiological model.

10. The method of claim 1, wherein estimating the parameters include using a patient-specific attribute including gender, age, weight, ethnicity, or comorbidity.

11. The method of claim 1, wherein the at least one blood characteristic includes at least one of a relative blood volume, a blood volume monitor (BVM) measurement, a hematocrit measurement, or a hemoconcentration measurement.

* * * * *